United States Patent
Mielekamp et al.

(10) Patent No.: US 7,991,105 B2
(45) Date of Patent: Aug. 2, 2011

(54) VISUALIZATION OF 3D IMAGES IN COMBINATION WITH 2D PROJECTION IMAGES

(75) Inventors: Pieter Maria Mielekamp, Veldhoven (NL); Robert Johannes Frederik Homan, Batenburg (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 110 days.

(21) Appl. No.: 12/445,750

(22) PCT Filed: Oct. 10, 2007

(86) PCT No.: PCT/IB2007/054126
§ 371 (c)(1),
(2), (4) Date: Apr. 16, 2009

(87) PCT Pub. No.: WO2008/047270
PCT Pub. Date: Apr. 24, 2008

(65) Prior Publication Data
US 2010/0296623 A1    Nov. 25, 2010

(30) Foreign Application Priority Data

Oct. 17, 2006   (EP) .................................... 06122432

(51) Int. Cl.
*A61B 6/00*    (2006.01)
(52) U.S. Cl. .......................................................... 378/4
(58) Field of Classification Search ............... 378/4, 98, 378/98.8, 98.11, 98.12
See application file for complete search history.

(56) References Cited

U.S. PATENT DOCUMENTS

| | | | |
|---|---|---|---|
| 4,777,956 A | | 10/1988 | Macovski |
| 5,376,795 A | * | 12/1994 | Hasegawa et al. ....... 250/363.04 |
| 5,490,218 A | * | 2/1996 | Krug et al. .................... 382/100 |
| 5,951,475 A | * | 9/1999 | Gueziec et al. ............... 600/425 |
| 6,078,638 A | * | 6/2000 | Sauer et al. ........................ 378/4 |
| 6,351,513 B1 | * | 2/2002 | Bani-Hashemi et al. ......... 378/8 |
| 6,389,104 B1 | | 5/2002 | Bani-Hashemi et al. |
| 6,539,074 B1 | * | 3/2003 | Yavuz et al. ...................... 378/4 |
| 6,711,433 B1 | * | 3/2004 | Geiger et al. ................. 600/431 |
| 2002/0045817 A1 | * | 4/2002 | Ichihashi ....................... 600/425 |
| 2003/0163038 A1 | * | 8/2003 | Simon et al. .................. 600/425 |
| 2004/0215071 A1 | * | 10/2004 | Frank et al. ................... 600/407 |
| 2005/0074084 A1 | * | 4/2005 | Wang et al. ....................... 378/4 |
| 2006/0036167 A1 | | 2/2006 | Shina |
| 2007/0129627 A1 | | 6/2007 | Profio et al. |
| 2008/0192996 A1 | * | 8/2008 | Timmer et al. ............... 382/128 |

FOREIGN PATENT DOCUMENTS

| | | |
|---|---|---|
| DE | 102005059804 A1 | 7/2007 |
| DE | 102006003126 A1 | 8/2007 |
| WO | 03077202 A1 | 9/2003 |
| WO | 2004093683 A1 | 11/2004 |
| WO | 2006056909 A1 | 6/2006 |
| WO | 2006095324 A1 | 9/2006 |

* cited by examiner

*Primary Examiner* — Edward J Glick
*Assistant Examiner* — Alexander H Taningco

(57) ABSTRACT

Original 2D rotational projections are combined preferably in an overlaying manner with corresponding viewings of a 3D reconstruction. By showing the 2D rotational projections in combination with the 3D reconstruction, 3D vessel information can be compared with the original 2D rotational image information over different rotational angles. In a clinical setup the combined visualization will allow for an easy check if findings in the 3D RA volume such as stenosis or aneurysms are not overestimated or underestimated due to e.g. an incomplete filling with contrast agent and/or a spectral beam hardening during the rotational scan.

20 Claims, 4 Drawing Sheets

VISUALIZATION OF 3D IMAGES IN COMBINATION WITH 2D PROJECTION IMAGES

FIELD OF INVENTION

The present invention generally relates to the field of digital image processing, in particular for medical purposes in order to enhance the visualization of acquired projection datasets of an object under examination. In particular, the present invention relates to the segmentation and visualization of rotational angiographic information, which are obtained by means of three-dimensional rotational angiography (3D RA), which is very useful for interventional radiology, especially in the field of endovascular therapy.

Specifically, the present invention relates to a method for displaying images of an object under examination, wherein a series of two-dimensional (2D) projection datasets of the object under examination is acquired at various projection angles and a three-dimensional (3D) representation of the object under examination is reconstructed based on the acquired 2D projection datasets.

Further, the present invention relates to a data processing device and to a medical X-ray examination apparatus, in particular a C-arm system or a computed tomography system, comprising the described data processing device, which is adapted for displaying images of an object under examination, in particular for displaying medical X-ray images of a patient under examination.

Furthermore, the present invention relates to a computer-readable medium and to a program element having instructions for executing the above-mentioned method for displaying images of an object under examination, in particular for displaying medical X-ray images of a patient under examination.

ART BACKGROUND

The imaging of body volumes and internal parts of a live subject is practiced notably in the field of medical diagnostics and therapy, that is, in the context of X-ray fluoroscopy. Therefore, the X-ray projection of a biological body volume will be considered hereinafter by way of example, but the present invention is not intended to be restricted thereto and can be used in all fields of application with similar conditions.

An angiogram is usually produced in order to diagnose and treat diseases of a patient's vascular system. An angiogram is a two-dimensional or three-dimensional image which shows the vascular tree or part thereof either on its own or emphasized with respect to the background. Angiograms are typically produced by means of an X-ray apparatus and with injection of an X-ray contrast agent.

Recent developments in particular of the mechanical framework of C-arm systems have improved the mechanical precision of X-ray scanning systems being attached to a C-arm such that 3D reconstructions of an object under examination have become possible. The X-ray scanning system comprises an X-ray source and an X-ray detector being arranged vis-à-vis with respect to each other. A 3D reconstruction may be based exclusively on a variety of 2D X-ray projection images obtained with the X-ray scanning system while moving around the object under examination in a rotational manner.

WO 2004/093683 discloses an apparatus and a method for a joint 3D display of an angiogram of a vascular system and local intravascular images. The angiogram is recorded by means of an X-ray apparatus, while the local intravascular images are generated by an ultrasound probe on a catheter. The position of the probe is determined by a position determination unit and is used to assign the recorded volume to the angiogram. The angiogram and the local intravascular image may be displayed in an overlapping manner in the same image. A physician can therefore link the information from the local intravascular image and from the angiogram at a glance and in a particularly intuitive manner.

U.S. Pat. No. 4,777,956 discloses a NMR angiography system, which is adapted to combine the isolated vessel image with a projection image of the anatomy. For example, the vessels can be displayed as a color overlay on a black and white anatomical image.

WO 03/077202 A1 discloses techniques for combining various types of diagnostic images to allow a user to view more useful information. In one embodiment, a composite image is obtained by fusing multi-planar reformat and maximum intensity projection images or minimum intensity projection images obtained from a CT scan. The maximum intensity projection image is obtained from a positron emission tomography scan. The resulting superimposed images can help a physician to see the diagnostic information in context.

There may be a need for providing an improved visualization of 3D images of an object under examination.

SUMMARY OF THE INVENTION

This need may be met by the subject matter according to the independent claims. Advantageous embodiments of the present invention are described by the dependent claims.

According to a first aspect of the invention there is provided a method for displaying images of an object under examination, in particular for displaying medical X-ray images of a patient under examination. The provided method comprises (a) acquiring a series of 2D projection datasets of the object under examination at various projection angles, (b) generating respectively one 2D image from respectively one of the acquired 2D projection datasets, (c) reconstructing a 3D representation of the object under examination based on the acquired 2D projection datasets, (d) displaying a 3D image showing the 3D representation under a selected projection angle from the various projection angles, and (e) combining the displayed 3D image with a display of the 2D image corresponding to the selected projection angle.

This aspect of the invention is based on the idea that the combined display of both the 3D image i.e. a projection of the 3D representation of the object under examination with the corresponding 2D image can offer an easy check whether structures being visible within the 3D image are physically existent or are based on artifacts. Such artifacts, which significantly reduce the quality of 3D reconstruction volumes, may be categorized into two different types of artifacts:

A) Reconstruction artifacts: These artifacts are typically related to beam hardening effects and scatter problems. Thereby, beam hardening is caused by a variation of the spectral distribution of an X-ray beam propagating through an X-ray absorbing medium. Thereby, spectral fractions having a lower X-ray energy undergo a stronger attenuation compared to spectral fractions having a higher X-ray energy. Therefore, when propagating through an X-ray attenuating medium the spectral distribution of the X-ray beam is shifted towards higher X-ray energies. Scatter problems are caused because an X-ray absorbing material always also represents a material causing an unwanted scattering of X-rays. Scattered X-ray however deteriorate the 2D projection datasets because scattered X-rays superpose the X-ray signal being caused by X-rays penetrating the object under examination without any interaction. However, only these X-rays clearly reflect the X-ray attenuation of the object.

B) Acquisition Protocol Artifacts:

In 3D X-ray angiographic imaging prior to the acquisition of rotational 2D projection datasets contrast agent is selectively inserted via a catheter into an area of interest within the object under examination. After some initial time delay of typically one second the rotational X-ray exposure sequence is started. Thereby, the time dependant pixel enhancement at the X-ray detector is in general influenced by four factors: (a) The amount respectively the density of injected contrast solution, (b) the rate of the flow and pulsation, (c) the physiology of the patient and (d) the vessel capacity. The vessel capacity may cause for instance an incomplete filling of large aneurysms. In particular because of these four reasons the acquisition protocol respectively the timing of the application of contrast agent is an imported factor in image quality chain.

The described method may allow a physician to relate the reconstructed 3D volumes to the original 2D exposures such that the origin of the artifacts being present in the 3D volume presentation can be determined. Thereby, the physician can take into account that a reconstruction artifact will result in discrepancies between 2D and 3D information, while acquisition artifacts will have their effects in both 2D and 3D.

Bad respectively incomplete contrast fillings of vessels will lead to insufficient pixel enhancements, which will cause problems with voxel densities and end up as 3D vessel segmentatation respectively visualisation artifacts. The big difference with acquisition protocol artifacts between the 2D and 3D presentations is that in the 2D presentation the temporal information will reveal the artifacts like e.g. pulsation or an early wash-out of contrast agent, while in the 3D volumes this information is missing.

For each projection angle there may be acquired exactly one 2D image representing a projection image. A proper alignment of the combined 3D/2D image can be realized by using the same or the inverse viewing direction, which is dictated by the 2D data acquisition geometry.

It is not necessary that respectively one 2D image is generated from every one of the various projection angles. If it is clear beforehand, that a display of the 3D image is only necessary for e.g. a predetermined angular range of projection directions, it may be sufficient that 2D images are only generated from projection datasets, which correspond to that predetermined angular range. Of course, for reconstruction of the 3D representation preferably all of the before acquired projection datasets may be used.

The reconstruction procedure may be carried out by arbitrary known algorithm such as filtered back projection algorithms, which are commonly known in the field of 3D image processing. Therefore, it is not necessary to explain possible reconstruction procedures within this application in more detail.

It has to be mentioned that the acquired 2D projection datasets are the only datasets, which are necessary in order to successfully carry out the described method for displaying the images of the object under examination. In other words, all acquired 2D projection datasets may be obtained be means of one and the same examination apparatus, which is e.g. a computed tomography system or a C-arm system. Therefore, the described method for displaying images of an object under examination may be carried out with only one single X-ray imaging apparatus. No other image modalities are necessary for carrying out the provided method.

According to an embodiment of the invention the method further comprises (a) displaying a further 3D image showing the 3D representation under a further selected projection angle from the various projection angles, and (b) combining the displayed further 3D image with a further display of the 2D image corresponding to the further selected projection angle.

This may provide the advantage that the combined display can be carried out for various projection angles. Therefore, a rotation of the 3D representation of the object may be displayed in a movie like manner, wherein different projection views of the object are displayed one after the other. Thereby, always the corresponding 2D image being assigned to the actual projection view of the 3D representation will be displayed simultaneously.

Apart from allowing a panning of the combined 3D/2D image, the described display architecture will also allow for a magnification respectively a zooming of special regions of interest within the object under examination. This makes it even more easy to identify artifacts in the reconstructed 3D image because artifacts typically have a different strength when comparing the combined displays for different projection angles.

In other words a physician can check whether a 3D silhouette information within the 3D image really corresponds to the 2D contrast information for different viewing corrections. Specifically, when (a) at a first projection angle a certain contrast area is located e.g. within a vessel of a patient under examination and (b) at a second projection angle the contrast area is located outside the vessel the physician can conclude that the contrast area is an artifact, which is physically not existing within the object under examination.

According to a further embodiment of the invention (a) the 2D projection datasets of the object under examination are acquired within an angular range of 180° and (b) a combined display of the 3D representation and the corresponding 2D image is sequentially provided at projection angles within an angular range of 360°.

This may provide the advantage that even if the object under examination has to be sequentially viewed under all possible projection angles corresponding to a full rotational movement of the displayed 3D object, a reduced data acquisition is sufficient wherein only projection angles within 180° are used for acquiring projection data. This efficient method is based on the fact that two 2D projection data, which are obtained with opposite viewing directions, represent the same information regarding the attenuation of the radiation having fully penetrated the object under examination.

In other words by reversing (a) the 3D viewing direction and (b) the perspective transformation of a view from opposite directions, each of the 2D images within an 360° angular viewing range can be created by re-using respectively mirroring a corresponding 2D image being obtained at a viewing direction having an angular offset of 180°. Furthermore, toggling the 3D viewing direction each 180° will allow for displaying a continuous full 360° movie of a rotational scan in a clockwise or in a counter clockwise direction by looping over the acquired images.

It has to be mentioned that in reality the 2D projection data acquisition should be carried out within an angular range being slightly larger than 180°. Thereby, one should take into account the angular spread of the radiation beam penetrating the object under examination.

According to a further embodiment of the invention the step of combining the displayed 3D image with a display of the 2D image comprises overlaying the displayed 3D image with a display of the 2D image. This may provide the advantage that a user trying to identify structural characteristics respectively abnormalities within the object under examination will be provided with all necessary information within one single view. Therefore, a distinction between reconstruction artifacts and real existent structural abnormalities will be significantly facilitated.

It has to be pointed out that apart from an overlay of the 3D image with the 2D image the two images can also be displayed also on the same screen e.g. next to each other or above each other.

According to a further embodiment of the invention (a) the displayed 3D image is illustrated with a first color and (b) the displayed 2D image is illustrated with a second color being different from the first color. Using different colors makes it more easy for a user to distinguish whether a visible characteristic is assigned to the 3D image or to the 2D image.

According to a further embodiment of the invention (a) the displayed 3D image is illustrated with a first structural design and (b) the displayed 2D image is illustrated with a second structural design being different from the first structural design. This may provide the advantage that a user can easily identify to which image a visible characteristic is assigned to even when the two overlaid images are displayed in the same color. This is in particular advantageous if the overlaid images are displayed on a monochrome screen or are printed on a paper by means of a black and white printer only.

According to a further embodiment of the invention the step of displaying a 3D image showing the 3D representation comprises using a 3D volume silhouette presentation. This may provide a very clear display of the combined 3D/2D image such that also minor abnormalities can be identified by a user in a reliable manner.

It has to be pointed out that for a flexible presentation of the described combined visualization of 3D and 2D images, an interactive threshold checking respectively a fine tuning of thresholds may be used, which thresholds are used for a segmentation of the acquired information. Thereby, image information regarding non-relevant parts of the image can be abolished.

A 3D volume silhouette presentation may be carried out e.g. by means of an image processing system for displaying an image of a body volume. Such an image processing system may comprise silhouette rendering means for generating a direct volume silhouette rendering of 3D image data, whereby the silhouette rendering is comprised of values proportional to the translucency of voxels of the 3D image data. Further, the image processing system may comprise means for varying the levels of contrast and/or shading in the silhouette rendering. Further, the image processing system may comprise control means for enabling a user to select and control the levels of contrast and/or shading in the silhouette rendering. Thereby, the control means may comprise analogue control means. Further, the image processing system may comprise edge enhancement means in order to emphasize silhouette contrast. Thereby, the edge enhancement means may comprise a convolution filter. Further, the image processing system may comprise means for performing an intensity correction in respect of a silhouette rendering for display so as to enable the darkness level of structures in the body volume to be controlled while maintaining the brightness of the silhouette. Further, the image processing system may be adapted to implement direct volume silhouette rendering performed by the silhouette rendering means by raycasting or by means of rendering textured slices through the volume of voxel densities in a back-to-front or front-to-back sorting order.

According to a further embodiment of the invention the 2D projection datasets are angiographic datasets such that both the 2D images and the 3D image are angiographic images. By applying the described method a 3D vessel anatomy respectively a pathology in the vessel system can be visualized very effectively. When comparing different combined 3D/2D images at different viewing angles, a physician is able to identify for instance so-called pseudo-stenosis artifacts on the 3D vessel tree, which pseudo-stenosis artifacts may occur in the neighborhood of coiled aneurysms or other dense material exhibiting a large X-ray attenuation and/or a strong X-ray scattering. Thereby, in a 3D reconstruction of the object under examination biological material being located behind a strongly absorbing material is often not reconstructed correctly. Therefore, such artifacts often cause inconsistencies of 2D rotational vessel projection images obtained at different viewing angles in particular due to X-ray beam hardening and unwanted X-ray scattering. The reasons of spectral beam hardening and X-ray scattering have already been described above.

It has to be emphasized that by combining the reconstructed 3D volume to the original 2D exposures also acquisition protocol artifacts can be identified. The origin of acquisition protocol artifacts has also already been explained above.

According to a further embodiment of the invention the method further comprises a segmentation of the 3D representation in relevant regions, which are supposed to be displayed, and non-relevant regions, which are supposed not to be displayed. This may provide the advantage that a very detailed and structured visualization of the vessel tree of a patient under examination can be obtained. Thereby, regions of the patient's body being outside of the vessel tree can be erased from the 3D representation.

It has to be mentioned that in principle also a segmentation of the generated 2D images is possible in order to improve the visibility of the final combined 3D/2D images. However, it has turned out that a segmentation of the 3D representation is the most effective way in order to improve the visibility of the final combined 3D/2D images.

According to a further embodiment of the invention the segmentation threshold is varied depending on an analysis of a final combined 3D/2D image being obtained from combining the displayed further 3D image with a further display of the 2D image corresponding to the further selected projection angle. Thereby, the segmentation threshold can be selected manually or automatically.

In particular the automatic selection of appropriate segmentation thresholds may be based on the voxel density within the 3D representation. Thereby, the term "voxel density" means the X-ray attenuation value of the various voxels. A histogram analysis showing the distribution of the voxel densities may be used for obtaining an appropriate segmentation threshold.

In this context it is clear that when a plurality of final combined 3D/2D images have been obtained at various viewing respectively projection angles, at least some of these final combined 3D/2D images may be analyzed in order to obtain one or more segmentation thresholds, which may be used for a subsequent display of theses or of further final combined 3D/2D images.

According to a further embodiment of the invention the method further comprises processing the 2D images, wherein, based on image information of the 3D representation, within the 2D image there is at least identified a first region and a second region being spatially different from the first region, and wherein the first region and the second region are processed in a different manner. Thereby, the first region may be assigned to the inside of a vessel and the second region may be assigned to the outside of a vessel.

The processing of the 2D images may comprise applying different coloring, changing the contrast, changing the brightness, applying a feature enhancement procedure, applying an edge enhancement procedure and/or reducing the noise separately for image pixels located within the first region and for image pixels located within the second region.

According to a further aspect of the invention there is provided a data processing device for displaying images of an object under examination, in particular for displaying medical X-ray images of a patient under examination. The data processing device comprises (a) a data processor, which is adapted for performing exemplary embodiments of the above-described method and (b) a memory for storing the acquired 2D projection datasets of the object under examination and/or for storing the reconstructed 3D representation of the object under examination.

According to a further aspect of the invention there is provided a medical X-ray examination apparatus, in particular a C-arm system or a computed tomography system. The medical X-ray examination apparatus comprises the above-described data processing device.

According to a further aspect of the invention there is provided a computer-readable medium on which there is stored a computer program for displaying images of an object under examination, in particular for displaying medical X-ray images of a patient under examination. The computer program, when being executed by a data processor, is adapted for performing exemplary embodiments of the above-described method.

According to a further aspect of the invention there is provided a program element for displaying images of an object under examination, in particular for displaying medical X-ray images of a patient under examination. The program element, when being executed by a data processor, is adapted for performing exemplary embodiments of the above-described method.

The computer program element may be implemented as computer readable instruction code in any suitable programming language, such as, for example, JAVA, C++, and may be stored on a computer-readable medium (removable disk, volatile or non-volatile memory, embedded memory/processor, etc.). The instruction code is operable to program a computer or other programmable device to carry out the intended functions. The computer program may be available from a network, such as the WorldWideWeb, from which it may be downloaded.

It has to be noted that embodiments of the invention have been described with reference to different subject matters. In particular, some embodiments have been described with reference to method type claims whereas other embodiments have been described with reference to apparatus type claims. However, a person skilled in the art will gather from the above and the following description that, unless other notified, in addition to any combination of features belonging to one type of subject matter also any combination between features relating to different subject matters, in particular between features of the method type claims and features of the apparatus type claims is considered to be disclosed with this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

BRIEF DESCRIPTION OF THE DRAWINGS

FIG. 1b shows a perspective view of the X-ray swing arm shown in FIG. 1a.

DETAILED DESCRIPTION

Figure 1A:
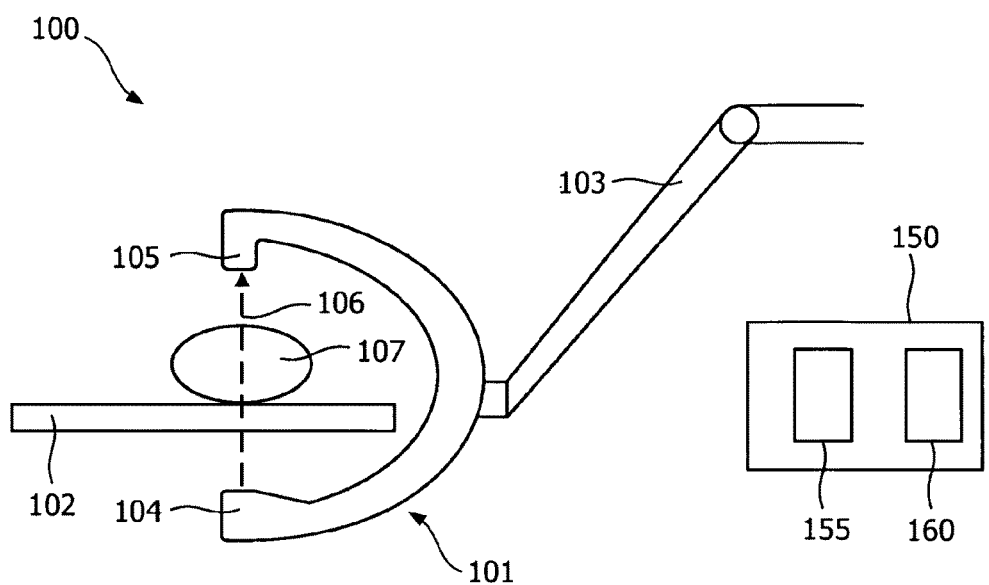
FIG. 1a shows a schematic side view of a medical C-arm system.

The illustration in the drawing is schematically. It is noted that in different figures, similar or identical elements are provided with the same reference signs or with reference signs, which are different from the corresponding reference signs only within the first digit.

Figure 1B:
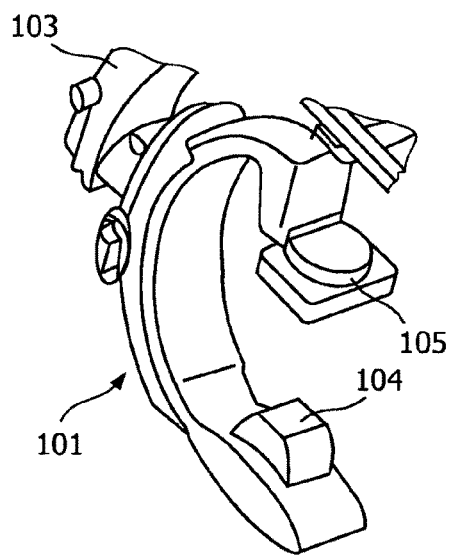

Referring to FIGS. 1a and 1b of the drawing, a medical X-ray imaging system 100 according to an embodiment of the invention comprises a swing arm scanning system (C-arm) 101 supported proximal a patient table 102 by a robotic arm 103. Housed within the swing arm 101, there is provided an X-ray tube 104 and an X-ray detector 105. The X-ray detector 105 is arranged and configured to receive X-rays 106, which have passed through a patient 107 representing the object under examination. Further, the X-ray detector 105 is adapted to generate an electrical signal representative of the intensity distribution thereof. By moving the swing arm 101, the X-ray tube 104 and the detector 105 can be placed at any desired location and orientation relative to the patient 107.

The C-arm system 100 further comprises a control unit 155 and a data processing device 160, which are both accommodated within a workstation or a personal computer 150. The control unit 155 is adapted to control the operation of the C-arm system 100. The data processing device 160 is adapted for collecting 2D projection images of the object 107 for the purpose of reconstructing a 3D representation of the object 107. Further, the data processing device 160 is adapted to overlay (a) a 3D image representing a viewing of the 3D representation under a selected projection angle with (b) a 2D projection image corresponding to the selected projection angle.

Figure 2:
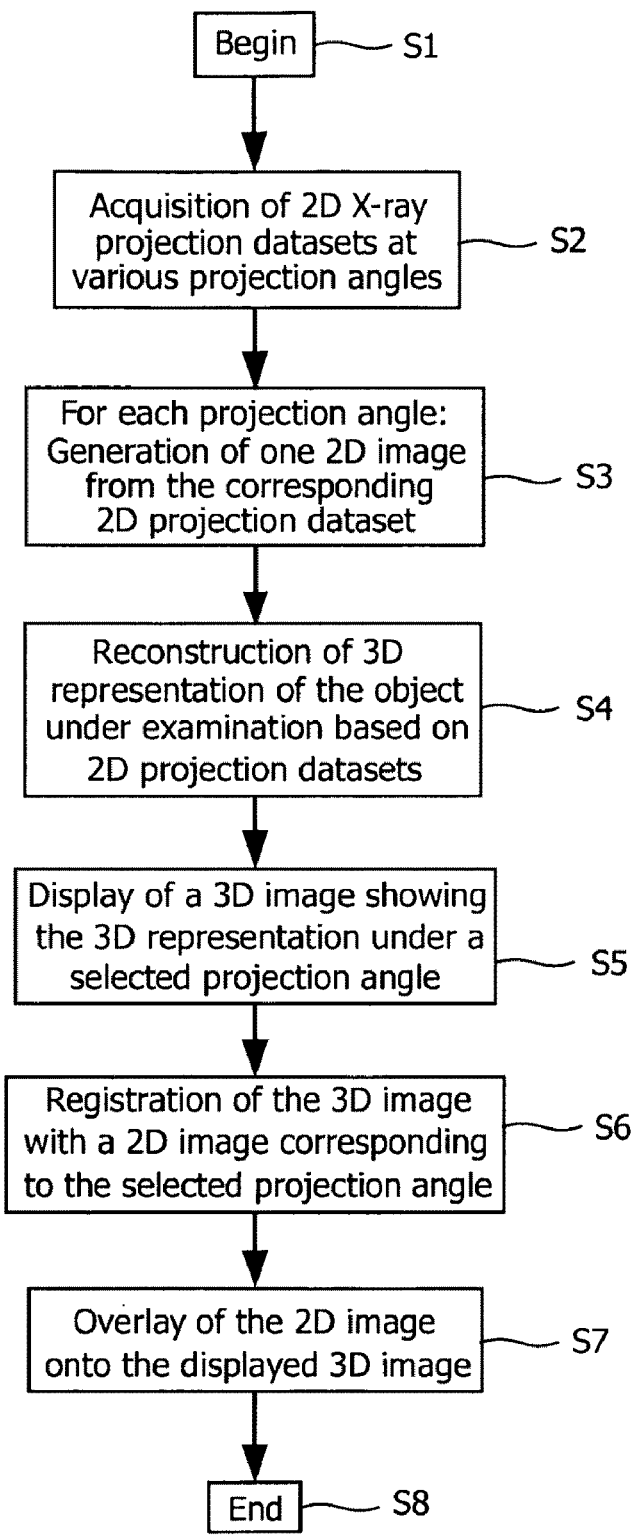
FIG. 2 shows a flow chart on a method for a combined visualization of a 3D image and a 2D image of an object under examination.

FIG. 2 shows a flow chart on an exemplary method for displaying a combined visualization of a 3D image and a 2D image of an object under examination. The described method starts with a step S1.

In step S2 there is acquired a series of 2D projection datasets of the object under examination at various projection angles. These datasets are obtained by recording the transversal X-ray attenuation profiles caused by the object under examination. Thereby, the X-ray detector measures the radiation intensity having penetrated the object. In order to reduce the fraction of scattered radiation reaching the X-ray detector, the detector may be equipped with a so-called anti scatter grid.

In step S3 there are generated 2D images based on the acquired 2D projection datasets. Thereby, respectively one 2D image is generated from exactly one of the acquired 2D projection datasets.

In step S4 there is performed a reconstruction procedure. Thereby, a 3D representation of the object under examination is reconstructed based on the acquired 2D projection datasets.

The reconstruction procedure may be carried out by arbitrary known algorithm such as filtered back projection algorithms, which are commonly known in the field of 3D image processing. However, also so-called iterative reconstruction procedures may be used, which provide the advantage that clear 3D reconstructions can be obtained even if the 2D projection datasets the reconstruction is based on comprise a comparatively big signal to noise ratio. A big signal to noise ratio typically is existent if the 2D projection datasets are acquired with a small radiation dose. However, iterative reconstruction procedures have the disadvantage that the computationally costs are typically higher compared to the computationally costs for standard reconstructions operating with filtered back projection algorithms.

In step S5 the reconstructed 3D representation is displayed. Thereby, an arbitrary viewing direction can be selected, which viewing direction is aligned with any one of the projection angles used before for acquiring one of the 2D projection datasets.

In step S6 an image registration is carried out. Thereby, one of the generated 2D images, which has been obtained at the same viewing angle as a forthcoming display of the 3D representation of the object, is aligned with the corresponding 3D image.

In step S7 the displayed 3D image is combined with a display of the 2D image corresponding to the selected projection angle. Thereby, the 3D image and the 2D image are overlaid with respect to each other. In order to allow a user to identify the two images different colors and/or different structures may be used.

It has to be mentioned that of course the combined display can be carried out for various projection angles. Therefore, a rotation of the 3D representation of the object may be displayed in a movie like manner, wherein different projection views of the object are displayed one after the other. Thereby, always the corresponding 2D image being assigned to the actual projection view of the 3D representation will be displayed simultaneously.

In order to show a 360° movie depicting the object under examination at all projection angles of the scanning unit rotating around the object, it may be sufficient to acquire 2D projection datasets only within an angular projection range of 180°. Thereby, one may take benefit from the fact that two 2D projection data, which are obtained at opposite viewing directions, represent the same information regarding the attenuation of the radiation having fully penetrated the object under examination. This means that by reversing (a) the 3D viewing direction and (b) the perspective transformation of a view from opposite directions, each of the 2D images within an 360° angular viewing range can be created be re-using respectively mirroring a corresponding 2D image being obtained at a viewing direction having an angular offset of 180°.

Finally, the described exemplary method ends with step S8.

FIGS. 3a, 3b, 3c and 3d show various images 330a, 330b, 330c and 330d depicting one and the same typical structure of a vessel tree 331 within a body of a patient. The vessel structure 331 is visible with a strong contrast compared to the tissue surrounding the vessel structure 331, because before acquiring a series of 2D X-ray projection datasets at different projection angles, a contrast fluid has been inserted in the vascular system of the patient.

Within the vessel tree 331 there is formed an aneurysma, which is filled with a coil 332. Typically, the coil has been inserted into the aneurysma in order to prevent a further blood flow into the aneurysma. Thereby, once the coil 332 has been inserted, the blood starts to coagulate and closes the aneurysma. Therefore, the blood pressure in the aneurysma is reduced such that a further widening of the aneurysma is prevented.

In order to allow a physician to extract more clinically relevant information from the images 330a, 330b, 330c and 330d, these images not only show a reconstructed 3D representation of the vessel tree 331 at a certain viewing angle. The images 330a, 330b, 330c and 330d also include a structured 2D illustration 334 of the vessel tree 331, which structured 2D illustration 334 has been overlaid onto the 3D representation of the vessel tree 331.

All depicted images 330a, 330b, 330c and 330d show the identical vessel tree structure 331. However, the image 330b shows the vessel tree 331 from an opposite direction as compared to the image 330a. This different orientation is indicated by the insert 335, which is depicted in the lower right corner of all the images 330a, 330b, 330c and 330d. The insert 335 directly gives an impression of the viewing direction of the vessel tree 331.

Figure 3A:
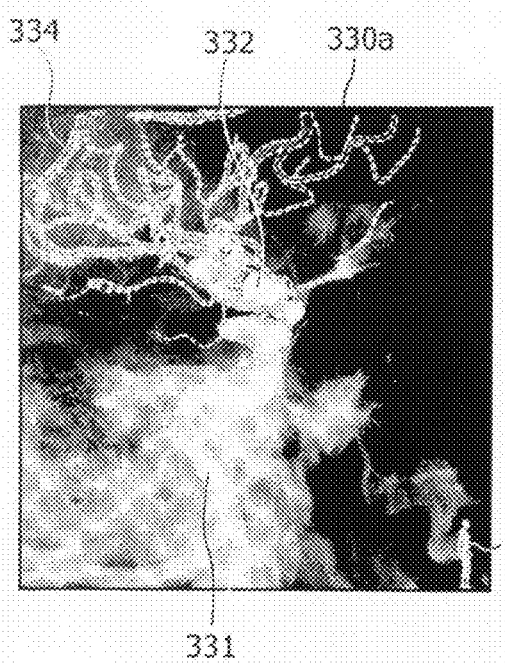
FIGS. 3a, 3b, 3c and 3d show overlaid 3D/2D images, which are generated by carrying out the method according to a preferred embodiment of the invention.
Figure 3B:
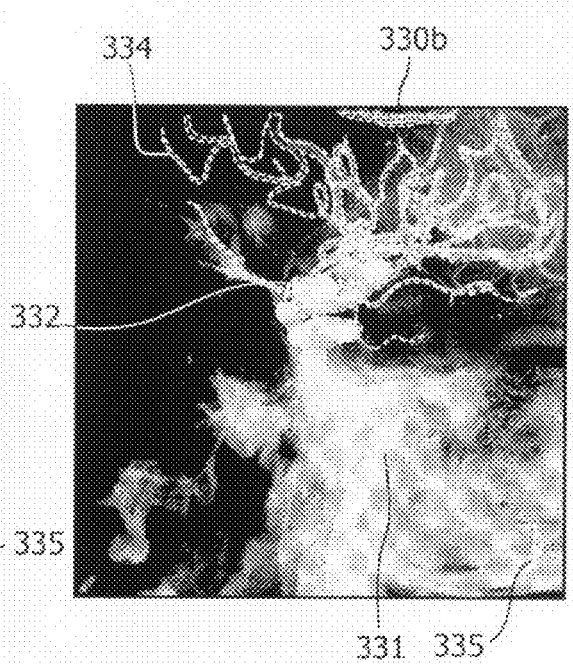
Figure 3C:
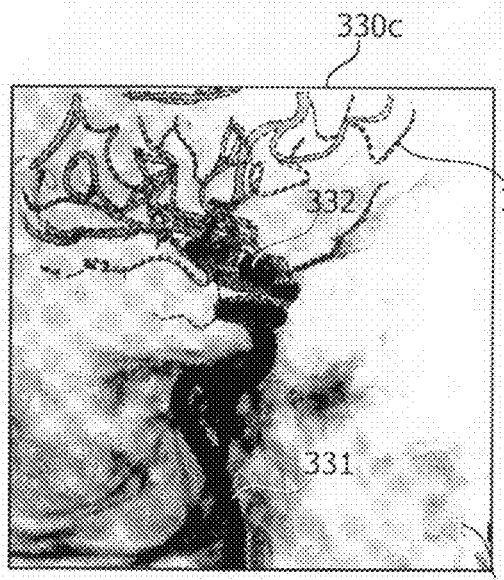
Figure 3D:
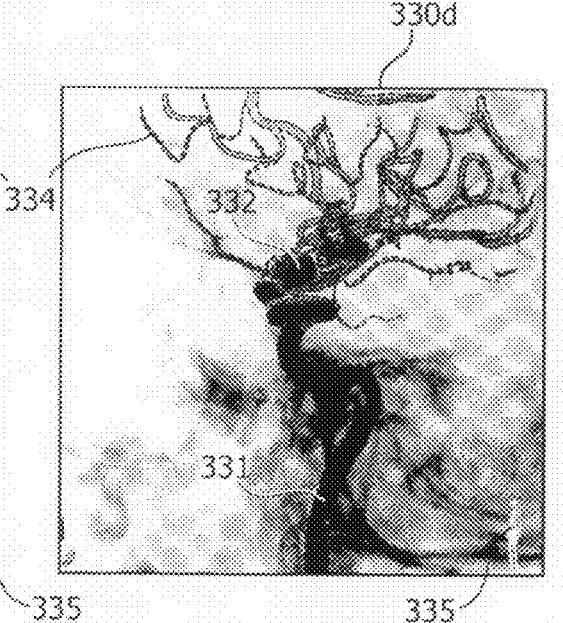

The images 330c and 330d show the vessel tree 331 at the same viewing directions as compared to the images 330a and 330b, respectively. However, as compared to the image 330a, the black and white polarity has been reversed. This means that image regions depicted in white in FIG. 3a and FIG. 3b are depicted in black in FIG. 3c and FIG. 3d, respectively. This demonstrates that by applying the improved visualization method a physician may be provided both with different projections views and different contrast such that best conditions are provided in order to give a reliable medical diagnosis.

The described combined visualization will offer an easy check if findings in the 3D RA volume such as stenosis or aneurysms are not over- or underestimated due to incomplete filling and/or spectral beam hardening during a rotational scan of the object under examination. Furthermore in a clinical set-up it will allow studying the effect of different injection settings and the acquisition protocols on the 3D reconstruction quality.

Figure 4:
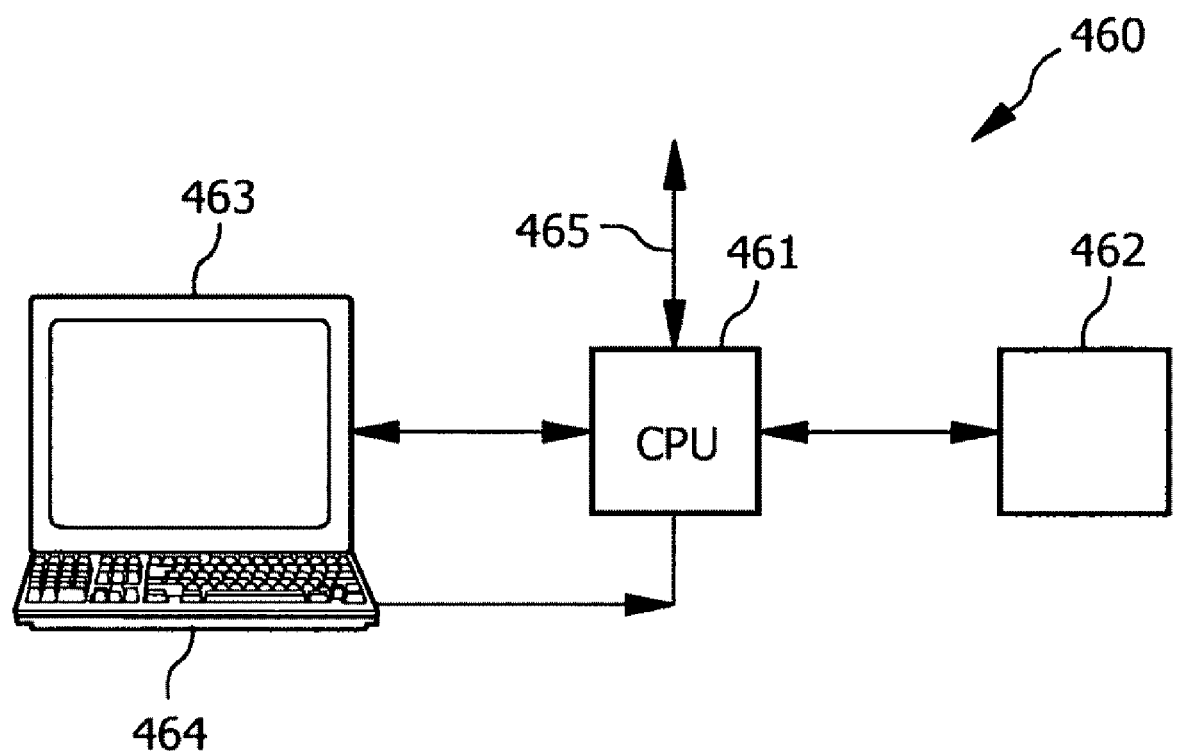
FIG. 4 shows an image-processing device for executing the preferred embodiment of the invention.

FIG. 4 depicts an exemplary embodiment of a data processing device 425 according to the present invention for executing an exemplary embodiment of a method in accordance with the present invention. The data processing device 425 comprises a central processing unit or image processor 461. The image processor 461 is connected to a memory 462 for temporally storing acquired or processed datasets. Via a bus system 465 the image processor 461 is connected to a plurality of input/output network or diagnosis devices, such as a CT scanner and/or a C-arm being used for 3D RA and for 2D X-ray imaging. Furthermore, the image processor 461 is connected to a display device 463, for example a computer monitor, for displaying images representing combined respectively overlaid 3D/2D images, which have been produced by the image processor 461. An operator or user may interact with the image processor 461 via a keyboard 464 and/or via any other input/output devices.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

In order to recapitulate the above described embodiments of the present invention one can state: It is described an improved visualization of an object under examination 107. Thereby, original 2D rotational projections are combined preferably in an overlaying manner with corresponding viewings of a 3D reconstruction. By showing the 2D rotational projections in combination with the 3D reconstruction, 3D vessel information can be compared with the original 2D rotational image information over different rotational angles. In a clinical setup the combined visualization will allow for an easy check if findings in the 3D RA volume such as stenosis or aneurysms are not overestimated or underestimated due to e.g. an incomplete filling with contrast agent and/or a spectral beam hardening during the rotational scan.

LIST OF REFERENCE SIGNS 100 medical X-ray imaging system/C-arm system
101 swing arm scanning system/C-arm
102 patient table
103 robotic arm
104 X-ray tube
105 X-ray detector
106 X-ray
107 object under examination/patient
150 workstation/personal computer
155 control unit
160 data processing device
S1 step 1
S2 step 2
S3 step 3
S4 step 4
S5 step 5
S6 step 6
S7 step 7
S8 step 8
330a typical roadmapping image
331 vessel tree
332 coil inserted in an aneurysma
334 structured 2D illustration of the vessel tree 331
335 insert indicating the orientation of the depicted roadmapping image
460 data processing device
461 central processing unit/image processor
462 memory
463 display device
464 keyboard
465 bus system

The invention claimed is:

1. A method for displaying images of an object under examination, the method comprising
   acquiring a series of 2D projection datasets of the object under examination at various projection angles,
   generating respectively one 2D image from respectively one of the acquired 2D projection datasets,
   reconstructing a 3D representation of the object under examination based on the acquired 2D projection datasets,
   displaying a 3D image showing the 3D representation under a selected projection angle from the various projection angles, and
   combining the displayed 3D image with a display of the 2D image corresponding to the selected projection angle.

2. The method according to claim 1, further comprising
   displaying a further 3D image showing the 3D representation under a further selected projection angle from the various projection angles, and
   combining the displayed further 3D image with a further display of the 2D image corresponding to the further selected projection angle.

3. The method according to claim 2, wherein
   the 2D projection datasets of the object under examination are acquired within an angular range of 180° and a combined display of the 3D representation and the corresponding 2D image is sequentially provided at projection angles within an angular range of 360°.

4. The method according to claim 1, wherein
   combining the displayed 3D image with a display of the 2D image comprises
   overlaying the displayed 3D image with a display of the 2D image.

5. The method according to claim 4, wherein
   the displayed 3D image is illustrated with a first color and the displayed 2D image is illustrated with a second color being different from the first color.

6. The method according to claim 4, wherein
   the displayed 3D image is illustrated with a first structural design and
   the displayed 2D image is illustrated with a second structural design being different from the first structural design.

7. The method according to claim 1, wherein
   displaying a 3D image showing the 3D representation comprises
   using a 3D volume silhouette presentation.

8. The method according to claim 1, further including:
   prior to acquiring the series of 2D projection data sets, injecting the patient with a contrast agent such that the 2D projection datasets are angiographic datasets such that both the 2D images and the 3D image are angiographic images.

9. The method according to claim 8, further comprising
   segmenting the 3D representation in relevant regions, which are supposed to be displayed, and non-relevant regions, which are supposed not to be displayed.

10. The method according to claim 8, wherein within the 2D image there is at least identified a first region and a second region being spatially different from the first region, and further including:
    processing the first region and the second region of the 2D image in a different manner.

11. A data processing device for displaying images of an object under examination the data processing device comprising
    a data processor, which is configured to perform the method as set forth in claim 1, and
    a memory which stores the acquired 2D projection datasets of the object under examination and the reconstructed 3D representation of the object under examination.

12. A medical X-ray examination apparatus, the medical X-ray examination apparatus comprising
    an x-ray tomography system which generates the series of 2D projection data sets, and
    the data processing device according to claim 11.

13. A non-transitory computer-readable medium on which there is stored a computer program which, when being executed by a data processor performs the method as set forth in claim 1.

14. A method of verifying if stenoses or aneurysms in a 3D angiography volume are overestimated or underestimated due to incomplete filling with a contrast agent and/or spectral beam hardening, the method comprising:
    after injecting a patient to be examined with a contrast agent, acquiring a series of 2D contrast agent enhanced projection data sets of the patient from a series of projection angles with a diagnostic imaging device;
    generating a series of 2D contrast agent enhanced images, each 2D contrast agent enhanced image being generated from a corresponding one of the 2D datasets and representing a projection for the corresponding one of the series of projection angles;

reconstructing the contrast agent enhanced image data sets into a 3D contrast agent enhanced image of the patient;

generating a 2D image of the 3D contrast agent enhanced image viewed from a selected one of the projection angles;

combining the 2D image of the 3D contrast agent enhanced image with the 2D contrast agent enhanced image corresponding to the selected one of the projection angles to generate a combined 2D contrast agent enhanced image;

displaying the combined 2D contrast agent enhanced image on a display device.

15. A system comprising:

a data processor programmed to:
receive a series of 2D projection data set acquired at each of a corresponding series of projection angles,
reconstruct a 3D image from the series of 2D projection data sets,
reconstruct 2D projection images from the 2D projection datasets such that each 2D projection image corresponds to one of the series of projection angles,
combining one of the 2D projection images corresponding to a selected one of the projection angles with the 3D image viewed from said selected one of the projection angles to generate a combined image; and
a display device on which the combined image is displayed.

16. The system according to claim 15, further including:
a diagnostic imaging device which generates the series of projection data sets after the patient has been injected with a contrast agent.

17. The system according to claim 15, wherein the data processor is programmed to:
overlay the one of the 2D projection images with the 3D image viewed from the selected one of the projection angles to generate the combined image.

18. The system according to claim 15, wherein the data processor is further programmed to:
segment the 3D image.

19. The system according to claim 15, wherein the display unit displays at least one of the 3D image viewed from the selected projection angle and the 2D projection image corresponding to the selected projection angle.

20. The system according to claim 15, wherein the processor is further programmed to:
color the 3D image and the selected 2D projection image with colors.

* * * * *